US008946488B2

(12) United States Patent
Garel et al.

(10) Patent No.: US 8,946,488 B2
(45) Date of Patent: *Feb. 3, 2015

(54) METHOD FOR HYDROXYLATING PHENOLS AND PHENOL ETHERS

(75) Inventors: Laurent Garel, Lyons (FR); Stéphanie Normand, Saint-Genis-Laval (FR); Pascal Pitiot, Lyons (FR); Jean-Christophe Bigouraux, Dargoire (FR)

(73) Assignee: Rhodia Operations, Aubervilliers (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/118,082

(22) PCT Filed: May 15, 2012

(86) PCT No.: PCT/EP2012/058961
§ 371 (c)(1),
(2), (4) Date: Nov. 19, 2013

(87) PCT Pub. No.: WO2012/156381
PCT Pub. Date: Nov. 22, 2012

(65) Prior Publication Data
US 2014/0073818 A1    Mar. 13, 2014

(30) Foreign Application Priority Data

May 19, 2011  (FR) .................................... 11 54372

(51) Int. Cl.
C07C 37/08 (2006.01)
C07C 41/26 (2006.01)
C07C 37/60 (2006.01)

(52) U.S. Cl.
CPC ................ C07C 41/26 (2013.01); C07C 37/60 (2013.01)
USPC ...................................................... 568/768

(58) Field of Classification Search
None
See application file for complete search history.

(56) References Cited

U.S. PATENT DOCUMENTS

| 3,849,502 A | 11/1974 | Bourdin et al. |
| 6,479,680 B1 | 11/2002 | Bassler et al. |
| 2006/0217576 A1 | 9/2006 | Muller et al. |
| 2011/0087038 A1 | 4/2011 | Teles et al. |
| 2011/0152579 A1 | 6/2011 | Garel |
| 2012/0035397 A1 | 2/2012 | Garel |

FOREIGN PATENT DOCUMENTS

| DE | 19835907 A1 | 2/2000 |
| DE | 10320634 A1 | 11/2004 |
| FR | 2071464 A5 | 9/1971 |
| JP | 50-62940 A | 5/1975 |
| WO | WO 2009024446 A2 | 2/2009 |
| WO | WO 2009150125 A1 | 12/2009 |
| WO | WO 2010115784 A1 | 10/2010 |

OTHER PUBLICATIONS

Yube, Kunio, et al—"Control of selectivity in phenol hydroxylation using microstructured catalytic wall reactors", 2007, ScienceDirect, Applied Catalysis A: General, vol. 327, pp. 278-286, Elsevier, XP022146424; 9 pgs.
Bayer, Thomas, et al—"Don't be baffled by static mixers: How to select and size the correct static mixer", May 2003, Chemical Engineering Magazine, Feature Report; pp. 50-57; 8 pgs.

*Primary Examiner* — Brian J Davis
(74) *Attorney, Agent, or Firm* — Beatrice C. Ortego

(57) ABSTRACT

A method for hydroxylating phenols and phenol ethers using hydrogen peroxide and specifically, a method for hydroxylating phenol using hydrogen peroxide. The method for hydroxylating a phenolic substrate selected from a phenol or a phenol ether by reacting such phenolic substrate with hydrogen peroxide in the presence of an acid catalyst comprises the following steps, implemented consecutively or simultaneously: a first step consisting of mixing a phenolic substrate with a hydrogen peroxide solution under conditions in which the temperature is sufficient for the initial phenolic substrate to remain liquid and for minimizing the conversion rate of the hydrogen peroxide; a second step consisting of carrying out the phenolic substrate hydroxylation reaction under adiabatic conditions, the acid catalyst being added at the mixing stage and/or at the beginning of the hydroxylation reaction; and a third step, if necessary, consisting of recovering the hydroxylated product.

23 Claims, 7 Drawing Sheets

METHOD FOR HYDROXYLATING PHENOLS AND PHENOL ETHERS

The present application is a U.S. national stage entry under 35 U.S.C. §371 of International Application No. PCT/EP2012/058961 filed May 15, 2012, which claims priority to French Application No. 11.54372 filed on May 19, 2011, the whole content of this application being herein incorporated by reference for all purposes.

The present invention relates to a process for hydroxylating phenols and phenol ethers with hydrogen peroxide.

The invention is more particularly directed toward a process for hydroxylating phenol with hydrogen peroxide.

In the description that follows of the present invention, the term "phenol substrate" is used without preference to denote a phenol or a phenol ether.

The reaction for the hydroxylation of phenol with hydrogen peroxide leads to the production of two isomers, namely 1,4-dihydroxybenzene or hydroquinone (HQ) and 1,2-dihydroxybenzene or pyrocatechol (PC).

In the present text, the term "diphenol" denotes hydroquinone and pyrocatechol.

Hydroquinone is a product used in many fields of application as a polymerization inhibitor, an antioxidant in elastomers, or as a synthetic intermediate. Another field of application is photography.

Pyrocatechol is also a product that is widely used, especially as a polymerization inhibitor or antioxidant in elastomers, olefins, polyolefins or polyurethane or as a tanning agent.

On account of its complexing properties, pyrocatechol is also used as a chelating agent especially in the electronics field and as a corrosion inhibitor.

It also serves as an intermediate in numerous syntheses, especially those of fragrances, cosmetics, medicaments and pesticides.

It follows that hydroquinone and pyrocatechol are mass-consumption products manufactured on a large scale.

Thus, given the size of the manufacturing volumes, it is important for their manufacturing process to be ideally optimized, in particular in terms of production efficiency, energy efficiency and yield.

Hydroquinone and pyrocatechol are conventionally produced by hydroxylation of phenol with hydrogen peroxide, in the presence of an acid catalyst, a strong protic acid or a solid catalyst with acidic properties, for instance TS-1.

One of the well-known routes for preparing said diphenols consists, according to FR 2 071 464, in performing the hydroxylation of phenol with hydrogen peroxide, in the presence of a strong protic acid, for instance sulfuric acid, chlorosulfuric acid or perchloric acid, or sulfonic acids, for instance methane sulfonic acid, trifluoromethanesulfonic acid, toluenesulfonic acid or phenolsulfonic acid.

Hydrogen peroxide is used in the form of an aqueous solution.

Commercially sold hydrogen peroxide solution has a concentration of about 30%, which gives rise to drawbacks in the reaction since the presence of water slows down the reaction, and in the energy balance since this water must then be removed.

Recourse to more concentrated hydrogen peroxide solutions is desirable, but their use at the industrial scale is difficult since the risks of explosion are all the greater the higher the hydrogen peroxide concentration.

Moreover, phenol is always used in large excess relative to the amount of hydrogen peroxide. Thus, the hydrogen peroxide/phenol mole ratio generally ranges between 0.01 and 0.3.

The presence of a large excess of phenol imposes, at the end of the reaction, the need to separate it from the reaction medium in order to recycle it.

This excess cost is proportionately more reduced the higher the degree of conversion of the phenol.

However, when the phenol hydroxylation reaction is performed in a conventionally used mixing device, such as a stirred reactor or a cascade of stirred reactors, the degree of conversion of the phenol is kept relatively low (less than 5%) to ensure good reaction performance. When the degree of conversion of the phenol is increased to reach 15-20%, the yields of diphenols obtained are divided by two. Specifically, the yield lowers since the level of byproducts increases especially via degradation of the diphenols, on account of the consecutive oxidation reactions.

It is thus very advantageous to increase the degree of conversion of the phenol by maintaining the selectivity and/or the yield of hydroquinone and pyrocatechol.

Thus, the object of the present invention is to provide an improved process for preparing hydroquinone and pyrocatechol in terms of material balance and energy efficiency.

A process has now been found, and this is what constitutes the subject of the present invention, for hydroxylating a phenol or a phenol ether, by reacting said phenol or phenol ether with hydrogen peroxide, in the presence of an acid catalyst, characterized in that it comprises the following steps performed successively or simultaneously:
- a first step of mixing a phenol or a phenol ether with a hydrogen peroxide solution under conditions such that the temperature is sufficient for the starting phenol or phenol ether to remain liquid and for the degree of conversion of the hydrogen peroxide to be minimized,
- a second step consisting in performing the hydroxylation reaction of the phenol or phenol ether under adiabatic conditions; the acid catalyst being introduced into the mixing step and/or at the start of the hydroxylation reaction,
- a third step, if necessary, of recovery of the hydroxylated product.

Figure 1:
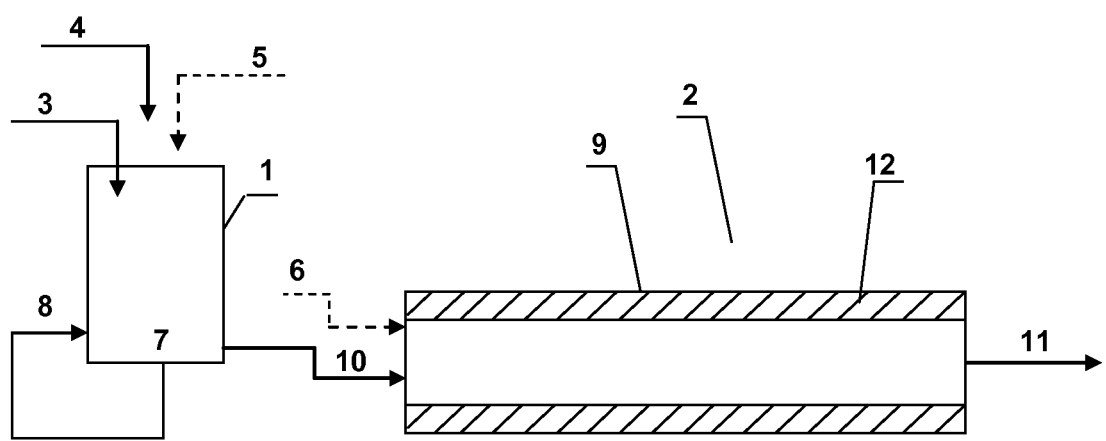
FIG. 1 is a schematic view of apparatus suitable for implementing the process of the invention, which comprises two assemblies: a first assembly comprising a jacketed stirred reactor equipped with means for introducing the reagents and a second assembly comprising a piston-flow reactor.
Figure 5:
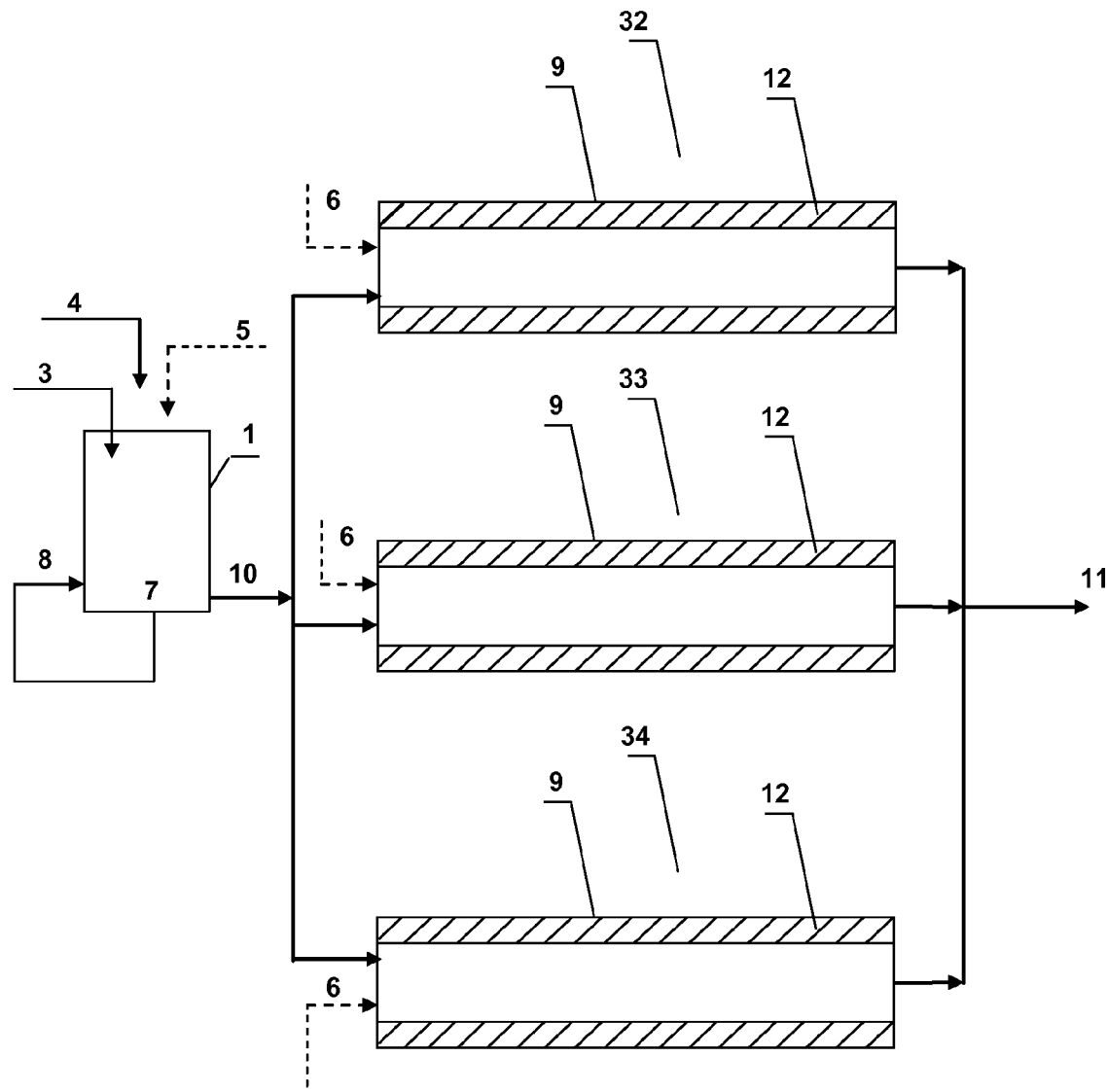

FIG. 5 is a schematic view of apparatus which comprises, as in FIG. 1, two assemblies, but in which the piston-flow reactor is replaced with an array of piston-flow reactors mounted in parallel, such apparatus being suitable for performing a variant of the process of the invention in which the hydroxylation step is performed in the array of piston-flow reactors mounted in parallel and working under adiabatic conditions.

Figure 6:
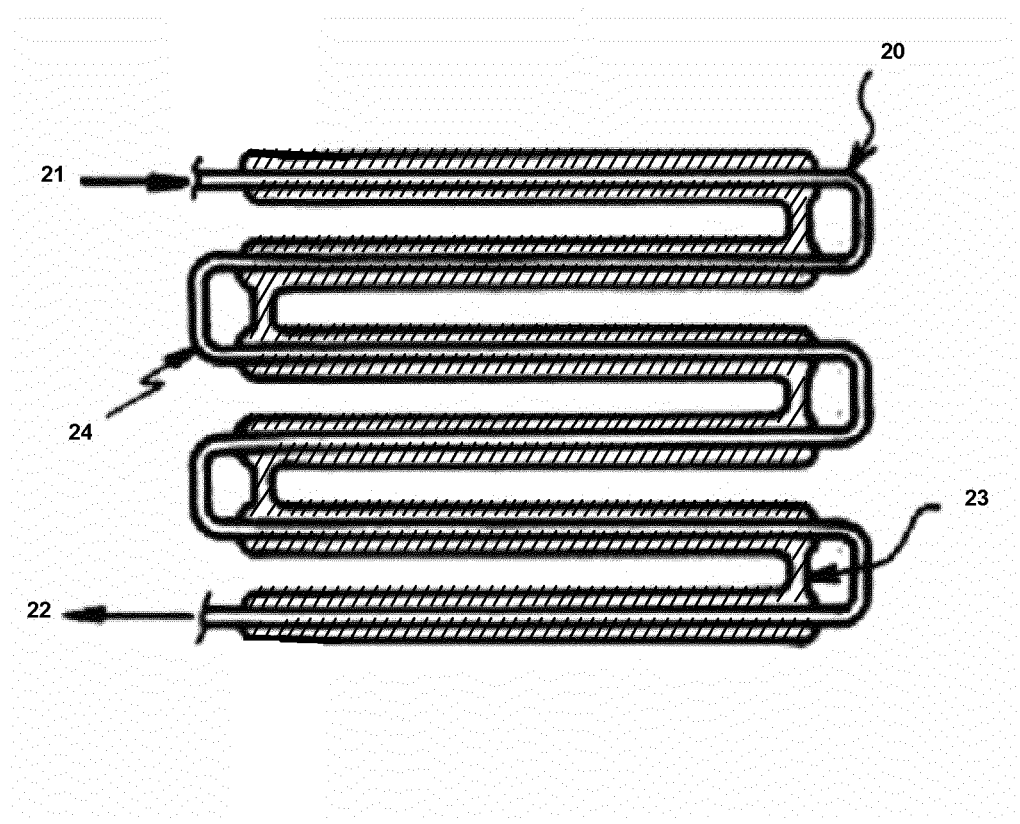

FIG. 6 illustrates a tubular reactor formed from concentric tubes that may be used as a piston-flow reactor in the hydroxylation reaction step according to the process of the invention.

Figure 7:
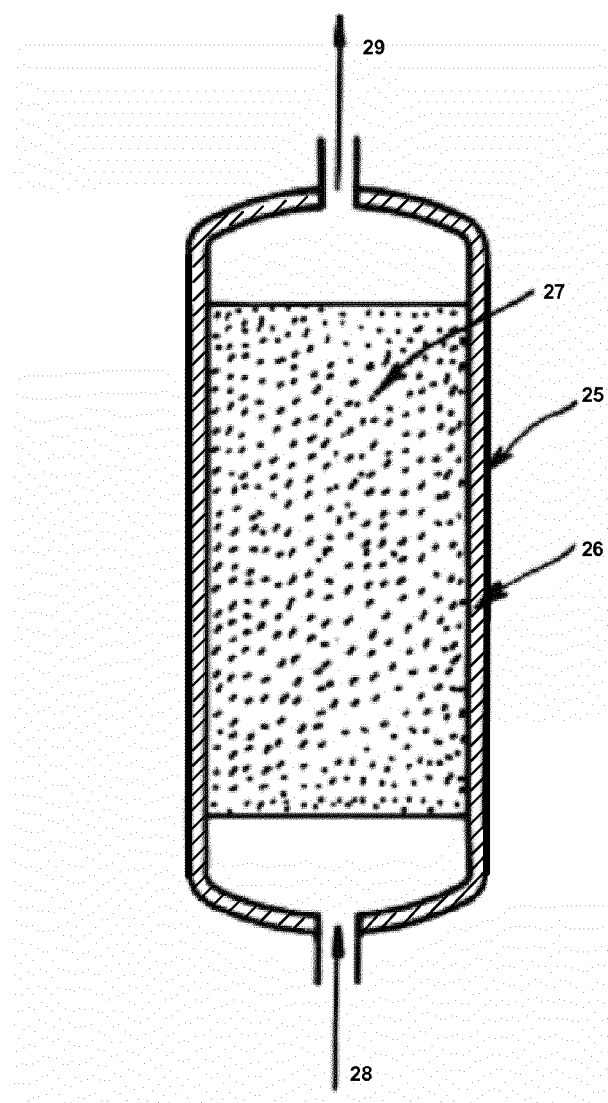

FIG. 7 illustrates a reactor in column form that may be used as the piston-flow reactor in the hydroxylation reaction step according to the process of the invention.

In the present text, the term "adiabatic conditions" means that the reaction is performed in an adiabatic chamber, i.e. in a chamber isolated from the external medium such that the reaction is performed without any external supply of energy. In other words, the hydroxylation reaction takes place without the reaction temperature being regulated by an external heat exchange.

Hitherto, it has never been described that a hydroxylation reaction can take place under adiabatic conditions. In particular, a hydroxylation reaction in a medium comprising a single liquid phase has never been disclosed in the prior art.

In accordance with the process of the invention, it has been found that performing the hydroxylation reaction under adiabatic conditions makes it possible to reduce the reaction time, for a given conversion and a given selectivity. This therefore leads to a significant increase in the production efficiency of the apparatus with, for example, in continuous mode, a reduction of the passage time of the reaction medium or a reduction of the volume of the apparatus.

The embodiments described in the text hereinbelow testify to the advantages obtained.

In accordance with the process of the invention, the phenolic compound is reacted with hydrogen peroxide in the presence of a catalyst and optionally of a cocatalyst.

The process of the invention is suitable for the hydroxylation of phenol or of a phenol ether, but also for substituted phenols or phenol ethers.

In the present text, the term "phenolic substrate" or "phenolic compound" is used to denote phenol, phenols and phenol ethers.

The term "substituted phenol or phenol ether" means a phenol or a phenol ether in which one of the hydrogen atoms of the aromatic ring is replaced with one or more substituents.

Generally, the term "several substituents" defines less than four substituents per aromatic nucleus.

Any substituent may be present, provided that it does not interfere in the reaction of the invention.

Thus, the process of the invention is suitable for being applied to phenolic substrates of general formula (I):

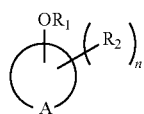

(I)

in which:
A symbolizes a benzene or naphthalene ring,
$R_1$ represents a hydrogen atom or an alkyl, cycloalkyl, aryl or aralkyl group,
$R_2$ represents a hydrogen atom or one or more identical or different substituents,
n, number of substituents per aromatic ring, is a number less than or equal to 4.

In formula (I) the group $OR_1$ is an ether group when $R_1$ is other than a hydrogen atom.

The number of substituents per aromatic ring is variable and generally less than or equal to 4, and preferably equal to 0, 1, 2 or 3.

Preferred examples of substituents are given for formula (Ia).

Thus, the process of the invention is suitable for phenolic substrates corresponding to formula (I) in which A represents a benzene ring and which are represented more particularly by the general formula (Ia):

(Ia)

in said formula:
n is a number from 0 to 4 and preferably equal to 0, 1, or 2,
$R_1$ represents a hydrogen atom or an alkyl, cycloalkyl, aryl or aralkyl group,
$R_2$, which may be identical or different, represent an alkyl group, an alkoxy group, a hydroxyl group, a halogen atom or a haloalkyl or perhaloalkyl group.

The process of the invention preferentially applies to substrates corresponding to formula (Ia) in which n is equal to 0 or 1; $R_1$ represents a hydrogen atom or an alkyl group containing from 1 to 4 carbon atoms; $R_2$ represents a hydrogen atom or an alkyl or alkoxy group containing from 1 to 4 carbon atoms.

In formulae (I) and (Ia), the term "alkyl" means a linear or branched $C_1$-$C_{15}$, preferably $C_1$-$C_{10}$ and even more preferentially $C_1$-$C_4$ hydrocarbon-based chain. Examples of preferred alkyl groups are especially methyl, ethyl, propyl, isopropyl, butyl, isobutyl and t-butyl.

The term "alkoxy" means a group alkyl-O— in which the term "alkyl" has the meaning given above. Preferred examples of alkoxy groups are methoxy or ethoxy groups.

The term "cycloalkyl" means a $C_3$-$C_8$ monocyclic cyclic hydrocarbon-based group, preferably a cyclopentyl or cyclohexyl group.

The term "aryl" means a monocyclic or polycyclic aromatic, preferably $C_6$-$C_{20}$ monocyclic or bicyclic group, preferably phenyl or naphthyl. When the group is polycyclic, i.e. when it comprises more than one cyclic nucleus, the cyclic nuclei may be fused in pairs or attached in pairs via σ bonds. Examples of ($C_8$-$C_{18}$)aryl groups are especially phenyl and naphthyl.

The term "aralkyl" means a linear or branched hydrocarbon-based group bearing a $C_7$-$C_{12}$ monocyclic aromatic ring, preferably benzyl: the aliphatic chain comprising 1 or 2 carbon atoms.

The term "haloalkyl group" means an alkyl group as defined previously in which one or more hydrogen atoms are replaced with a halogen atom, preferably a fluorine atom.

The term "perhaloalkyl group" means an alkyl group comprising from 1 to 10 carbon atoms and from 3 to 21 halogen atoms, preferably fluorine, and more particularly the trifluoromethyl group.

The term "halogen atom" defines fluorine, chlorine and bromine.

As illustrations of phenolic substrates of formula (I) that may be used in the process of the invention, mention may be made more particularly of:
those corresponding to formula (I) in which n is equal to 0, such as phenol or anisole,
those corresponding to formula (I) in which n is equal to 1, such as o-cresol, m-cresol, p-cresol, 2-ethylphenol, 3-ethylphenol, 2-propylphenol, 2-sec-butylphenol, 2-tert-butylphenol, 3-tert-butylphenol, 4-tert-butylphenol, 2-methoxyphenol, 3-methoxyphenol, 4-methoxyphenol, 2-ethoxyphenol, methyl salicylate, 2-chlorophenol, 3-chlorophenol or 4-chlorophenol, those corresponding to formula (I) in which n is equal to 2, such as 2,3-dimethylphenol, 2,5-dimethylphenol, 2,6-dimethylphenol, 3,5-dimethyphenol, 2,3-dichlorophenol, 2,5-dichlorophenol, 2,6-dichlorophenol, 3,5-dichlorophenol, 2,6-di-tert-butylphenol or 3,5-di-tert-butylphenol, those corresponding to formula (I) in which n is equal to 3, such as 2,3,5-trimethylphenol, 2,3,6-trimethylphenol, 2,3,5-trichlorophenol or 2,3,6-trichlorophenol, those corresponding to formula (I) in which A represents a naphthalene ring, such as 1-hydroxynaphthalene.

Among the abovementioned phenolic substrates, use is preferentially made of phenol, o-cresol, m-cresol, p-cresol, anisole, phenetole, 2-methoxyphenol (guaiacol) or 2-ethoxyphenol (guetol).

The present process is most particularly suitable for preparing hydroquinone and pyrocatechol from phenol.

A homogeneous catalyst which is a strong acid is used in the process of the invention. In the present invention, the term "strong acid" denotes an acid with a pKa in water of less than −0.1 and preferably less than −1.0.

The pKa is defined as being the ionic dissociation constant of the acid/base pair, when water is used as solvent.

Among the acids corresponding to this definition, it is preferable to use those that are stable with respect to oxidation with hydrogen peroxide.

Mention may be made more particularly of halogenated or non-halogenated oxy acids such as sulfuric acid, phosphoric acid, pyrosulfuric acid, perchloric acid; aliphatic or aromatic sulfonic acids, for instance methanesulfonic acid, ethanesulfonic acid, benzenesulfonic acid, bis-trifluoromethanesulfonimide, toluenesulfonic acids, naphthalenesulfonic acids, benzenedisulfonic acids, naphthalenedisulfonic acids; halosulfonic acids such as fluorosulfonic acid, chlorosulfonic acid or trifluoromethanesulfonic acid.

Among the abovementioned acids, sulfuric acid, perchloric acid, methanesulfonic acid, trifluoromethanesulfonic acid, toluenesulfonic acid, phenol sulfonic acid and bis-trifluoromethanesulfonimide are preferably used.

According to one variant of the process of the invention, it is possible to use as strong protic acid a hydroxyaromatic sulfonic acid as described in WO 2009/150 125.

As preferred examples of hydroxyaromatic sulfonic acids preferentially used in the process of the invention, mention may be made of the acids corresponding to the following formula:

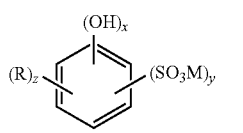
(Ia)

in said formula:
x is equal to 1, 2 or 3, preferably 1 or 2,
y is equal to 1 or 2,
z is a number from 0 to 4 and preferably equal to 0, 1, or 2,
M represents a hydrogen, sodium or potassium atom,
R represents an alkyl or alkoxy group containing from 1 to 4 carbon atoms or a carboxylic group.

Among the acids that are suitable for use in the process of the invention, mention may be made more particularly of hydroxybenzenesulfonic acids, sulfonated hydroxybenzoic acids; hydroxybenzenedisulfonic acids, dihydroxybenzenedisulfonic acids, hydroxytoluenesulfonic acids, hydroxynaphthalenesulfonic acids and hydroxynaphthalenedisulfonic acids, and mixtures thereof.

Among the hydroxybenzenesulfonic acids, use will preferably be made of 4-hydroxybenzenesulfonic acid, 2-hydroxybenzenesulfonic acid or 5-sulfosalicylic acid, or a mixture thereof.

As preferred examples of dihydroxybenzenesulfonic acids used, mention may be made of sulfonic acids resulting from the sulfonation of hydroquinone (1,4-dihydroxybenzene), of pyrocatechol (1,2-dihydroxybenzene) and of resorcinol (1,3-dihydroxybenzene).

The preferred dihydroxybenzenedisulfonic acids are 5,6-dihydroxy-1,3-benzenedisulfonic acid, 4,6-dihydroxy-1,3-benzenedisulfonic acid and 2,5-dihydroxy-1,4-benzenedisulfonic acid.

The sulfonic hydroxyaromatic acids are available in solid or liquid form or as an aqueous solution whose concentration may range between 5% and 95% by weight and preferably between 50% and 70% by weight.

According to another variant of the process of the invention, it is possible to use a mixture of at least two strong protic acids, as described in WO 2010/115 784.

The mixture comprises two acids (A) and (B) having specific respective pKa values: the acid (B) being much stronger than the acid (A).

Said mixture comprises:
a strong acid (A) with a p$K_a$ (S) greater than or equal to that of sulfuric acid and a Δp$K_a$ (S) relative to sulfuric acid of less than or equal to 4 and greater than or equal to 0, and another acid (B) chosen from superacids.

The acid (A) has a p$K_a$ (S) greater than or equal to that of sulfuric acid: (S) representing the organic solvent, which is nitrobenzene.

The acid (B) is a superacid, which is defined as having a p$K_a$ (S) less than that of sulfuric acid.

The p$K_a$ (S) is defined as being the ionic dissociation constant of the acid/base couple in a solvent (S).

The p$K_a$ of the acids is defined by reference to a potentiometry measurement performed in a solvent which is nitrobenzene (S), and the measuring protocol of which is described before the examples of WO 2010/115 784.

The acids used in said mixture are defined by a p$K_a$ difference, Δp$K_a$, which corresponds for the same solvent to the difference between the p$K_a$ of the chosen acid and the p$K_a$ of sulfuric acid.

The acid (A) used has a Δp$K_a$ (S) relative to sulfuric acid of less than or equal to 4 and greater than or equal to 0.

Even more preferentially, the acid (A) has a Δp$K_a$ (S) relative to sulfuric acid of less than or equal to 3 and greater than or equal to 0.

Examples of acids (A) that may especially be mentioned include sulfuric acid, aliphatic or aromatic sulfonic acids, for instance methanesulfonic acid, ethanesulfonic acid, benzenesulfonic acid, toluenesulfonic acids and naphthalenesulfonic acids.

Another class of acids (A) is that of hydroxybenzenesulfonic acids, sulfonated hydroxybenzoic acids; hydroxybenzenedisulfonic acids, dihydroxybenzenedisulfonic acids, hydroxytoluenesulfonic acids, hydroxynaphthalenesulfonic acids and hydroxynaphthalenedisulfonic acids, and mixtures thereof.

Among the abovementioned acids, the preferred acids are 4-hydroxybenzenesulfonic acid, 2-hydroxybenzene sulfonic acid, 5-sulfosalicylic acid, sulfonic acids resulting from the sulfonation of hydroquinone (1,4-dihydroxybenzene), of pyrocatechol (1,2-dihydroxybenzene) and of resorcinol (1,3-dihydroxybenzene); 5,6-dihydroxy-1,3-benzenedisulfonic acid, 4,6-dihydroxy-1,3-benzenedisulfonic acid and 2,5-dihydroxy-1,4-benzenedisulfonic acid.

Other examples of acids that may especially be mentioned include perhaloacetic acids such as trichloroacetic acid and trifluoroacetic acid.

As regards the second component (B) of the mixture of acids, it is a superacid, i.e. an acid with a $pK_a$ (S) lower than that of sulfuric acid and which thus has a negative $\Delta pK_a$.

The lower limit is not critical, but, generally, the $\Delta pK_a$ in nitrobenzene is greater than or equal to −12.

The superacids preferentially chosen have a $\Delta pK_a$ of less than or equal to −0.1 and preferably greater than or equal to −8.

Examples of superacids (B) that may be mentioned include perchloric acid, halosulfonic acids such as fluorosulfonic acid or chlorosulfonic acid; perhaloalkanesulfonic acids, preferably trifluoromethanesulfonic acid.

Superacids (B) that may also be mentioned include, inter alia, trifluoromethanesulfinic acid; bis-trifluoromethanesulfonimide.

As preferentially chosen pairs of acids (A) and (B), mention may be made of perchloric acid and sulfuric acid; perchloric acid and 4-hydroxybenzenesulfonic acid; trifluoromethanesulfonic acid and 4-hydroxybenzenesulfonic acid; bis-trifluoromethanesulfonimide and 4-hydroxybenzenesulfonic acid.

The proportion in the mixture of the various acids may vary widely.

Thus, use may be made of mixtures comprising:
from 60 mol % to 95 mol % and preferably from 80 mol % to 95 mol % of an acid (A),
from 5 mol % to 40 mol % and preferably from 5 mol % to 20 mol % of an acid (B).

Each percentage of acid expresses the ratio (expressed as a percentage) between the number of moles of the acid under consideration and the number of moles of the sum of the two acids (A) and (B).

The acids used in the mixture are commercially available in solid or liquid form or as an aqueous solution whose concentration may range between 5% and 95% by weight and preferably between 50% and 70% by weight.

The strong protic acid or the mixture of acids is used in the process of the invention in an amount, expressed by the ratio of the number of equivalents of protons to the number of moles of phenolic substrate, which advantageously ranges between 0.002% and 0.15%. Thus, said mole ratio is preferentially chosen between 0.01% and 0.07%.

According to another variant of the process of the invention, the hydroxylation of the phenolic substrate is performed in the presence of a cocatalyst, which is a ketone compound, and more particularly those corresponding to formula (II):

$$R_a\text{—CO—X—}R_b \quad (II)$$

in said formula (II):
$R_a$ and $R_b$, which may be identical or different, represent hydrocarbon-based groups containing from 1 to 30 carbon atoms or together form a divalent group, optionally substituted with one or more halogen atoms or functional groups that are stable under the reaction conditions, X represents a valency bond, a —CO— group, a —CHOH group or a group —(R)$_n$—: R representing an alkylene group preferably containing from 1 to 4 carbon atoms and n is an integer chosen between 1 and 16.

In formula (II), $R_a$ and $R_b$ more particularly represent:

linear or branched alkyl groups, linear or branched alkenyl groups, cycloalkyl or cycloalkenyl groups comprising from 4 to 6 carbon atoms, monocyclic or polycyclic aryl groups; in the latter case, the rings together forming an ortho- or ortho- and peri-fused system or being linked together via a valency bond, arylalkyl or arylalkenyl groups, $R_a$ and $R_b$ may together form an alkylene or alkenylene group comprising from 3 to 5 carbon atoms, optionally substituted with an alkyl group with low carbon condensation or with a cycloalkyl or cycloalkenyl group containing 4 to 6 carbon atoms; 2 to 4 of the carbon atoms of the alkylene or alkenylene groups possibly forming part of one or two benzene rings optionally substituted with 1 to 4 hydroxyl and/or alkyl and/or alkoxy groups with low carbon condensation.

In the description that follows of the invention, the term "alkyl group of low carbon condensation" means a linear or branched alkyl group generally containing from 1 to 4 carbon atoms.

The abovementioned hydrocarbon-based groups may be substituted with one or more, preferably 1 to 4, alkyl groups of low carbon condensation or functional groups such as hydroxyl groups, alkoxy groups of low carbon condensation, hydroxycarbonyl or alkyloxycarbonyl groups comprising from 1 to 4 carbon atoms in the alkyl group, a nitrile, sulfonic or nitro group, or with one or more halogen atoms, and especially chlorine and bromine.

Preferably, $R_a$ and $R_b$ more particularly represent:

linear or branched alkyl groups containing from 1 to 10 carbon atoms, linear or branched alkenyl groups containing from 2 to 10 carbon atoms, cycloalkyl or cycloalkenyl groups comprising from 4 to 6 carbon atoms, phenyl groups optionally substituted with 1 to 4 alkyl and/or hydroxyl and/or alkoxy groups, phenylalkyl or phenylalkenyl groups comprising 1 (or 2) to 10 carbon atoms in the aliphatic part, and even more particularly from 1 (or 2) to 5 carbon atoms in the aliphatic part, $R_a$ and $R_b$ may together form an alkylene or alkenylene group comprising from 3 to 5 carbon atoms, optionally substituted with 1 to 4 alkyl groups with low carbon condensation.

Thus, use is made most particularly of ketone compounds of dialkyl ketone type corresponding to formula (II) in which $R_a$ and $R_b$ represent a linear or branched alkyl group containing from 1 to 8 carbon atoms.

Among all the ketone compounds corresponding to formula (II), the ones that are preferentially chosen are those corresponding to formula (II) in which $R_a$ and $R_b$ represent an optionally substituted phenyl group.

Said ketone compounds may be represented by formula (IIa) below:

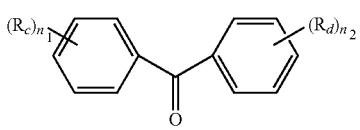

(IIa)

in said formula (IIa):
$R_c$ and $R_d$, which may be identical or different, represent a hydrogen atom or a substituent, preferably an electron-donating group,
$n_1$ and $n_2$, which may be identical or different, represent a number equal to 0, 1, 2 or 3,
optionally, the two carbon atoms located a to the two carbon atoms bearing the —CO group may be linked together via a valency bond or via a —$CH_2$— group, thus forming a ketone ring, which may be saturated, but also unsaturated.

The substituent is chosen such that it does not react under the acidity conditions of the invention. It is preferentially an electron-donating group.

The term "electron-donating group" means a group as defined by H. C. Brown in the book by Jerry March—Advanced Organic Chemistry, chapter 9, pages 243 and 244 (1985).

Examples of substituents that are suitable for use in the invention are the following:
linear or branched alkyl groups containing from 1 to 4 carbon atoms,
a phenyl group,
alkoxy groups comprising a linear or branched alkyl chain containing from 1 to 4 carbon atoms or a phenoxy group,
a hydroxyl group,
a fluorine atom.

As examples of ketone compounds that are particularly suitable for use in the invention, mention may be made most particularly of the ketone compounds corresponding to the general formula (IIa) in which $R_c$ and $R_d$, which may be identical or different, represent a hydrogen atom or a substituent as mentioned previously, preferably in position 4,4', and $n_1$ and $n_2$, which may be identical or different, are equal to 0 or 1.

Use is preferentially made of the ketone compounds corresponding to formula (IIa) in which $R_c$ and $R_d$, which may be identical or different, represent a hydrogen atom; a methyl, ethyl, tert-butyl or phenyl group; a methoxy or ethoxy group; a hydroxyl group, preferably in position 3,3' or 4,4'.

As specific examples of ketones that may be used in the process of the invention, mention may be made more particularly of:
benzophenone
2-methylbenzophenone
2,4-dimethylbenzophenone
4,4'-dimethylbenzophenone
2,2'-dimethylbenzophenone
4,4'-dimethoxybenzophenone
4-hydroxybenzophenone
4,4'-dihydroxybenzophenone
4-benzoylbiphenyl.

The amount of ketone compound used, expressed by the ratio between the number of moles of ketone compound and the number of moles of phenolic compound, may range between 0.01% and 20% and preferably between 0.1% and 2%.

In accordance with the process of the invention, a phenol or a phenol ether is reacted with hydrogen peroxide, in the presence of a strong protic acid and optionally of a ketone.

The hydrogen peroxide used according to the invention may be in the form of an aqueous solution or an organic solution.

Since the aqueous solutions are more readily commercially available, they are preferably used.

The concentration of the aqueous hydrogen peroxide solution, although not critical per se, is chosen so as to introduce as little water as possible into the reaction medium. An aqueous hydrogen peroxide solution with an $H_2O_2$ concentration of at least 20% by weight and preferably between 20% and 90% by weight is generally used.

An aqueous hydrogen peroxide solution with a weight concentration of $H_2O_2$ ranging from 30% to 90%, preferably from 30% to 70%, more preferably from 40% to 70% and even more preferably from 45% to 70% is advantageously chosen.

The amount of hydrogen peroxide may range up to 0.5 mol of $H_2O_2$ per 1 mol of substrate of formula (I).

However, in order to obtain an industrially acceptable yield, it is preferable to use a hydrogen peroxide/phenolic substrate mole ratio of from 0.01 to 0.3 and preferably from 0.03 to 0.10. The phenolic substrate also advantageously acts as solvent so as to avoid the use of other solvents, for example water.

Since the amount of water has an influence on the reaction rate, it is preferable to minimize its presence: water may be introduced into the reaction medium especially by the reagents used.

An initial water content of the medium of less than 20% by weight and preferably less than 10% by weight should preferentially be chosen.

The indicated weight contents of water are expressed relative to the mixture of substrate of formula (I)/hydrogen peroxide/water.

This initial water corresponds to the water introduced with the reagents and especially with the hydrogen peroxide.

One variant of the process of the invention consists in adding an agent for complexing the metal ions present in the medium since they are harmful to the correct procedure of the process of the invention, especially in the case of phenols in which the yields of hydroxylation products are low. Consequently, it is preferable to inhibit the action of the metal ions.

The metal ions that are harmful to the procedure of the hydroxylation are transition metal ions and more particularly iron, nickel, copper, chromium, cobalt, manganese and vanadium ions.

The metal ions are introduced by the reagents and especially the starting substrates and the apparatus used. To inhibit the action of these metal ions, it suffices to perform the reaction in the presence of one or more complexing agents that are stable with respect to hydrogen peroxide and which give complexes that cannot be decomposed with the strong acids present and in which the metal can no longer exert any chemical activity.

As nonlimiting examples of complexing agents, use may be made especially of the various phosphoric acids, for instance orthophosphoric acid, meta-phosphoric acid, pyrophosphoric acid, polyphosphoric acids, phosphonic acids such as (1-hydroxyethylidene)diphosphonic acid, phosphonic acid, ethylphosphonic acid or phenylphosphonic acid.

Use may also be made of esters of the abovementioned acids, and mention may be made more particularly of monoalkyl or dialkyl, monocycloalkyl or dicycloalkyl, or monoalkylaryl or dialkylaryl orthophosphates, for example ethyl or diethyl phosphate, hexyl phosphate, cyclohexyl phosphate or benzyl phosphate.

The amount of complexing agent depends on the metal ion content of the reaction medium.

There is obviously no upper limit, and the amount of complexing agents present may be largely in excess relative to that necessary to complex the metal ions. Generally, an amount representing from 0.01% to 2% and preferably from 0.01% to 0.3% by weight of the reaction medium is suitable for use.

In accordance with the process of the invention, the mixing of the reagents and the hydroxylation reaction are successively performed.

According to a first step of the process of the invention, the phenolic substrate and the hydrogen peroxide solution are placed in contact: the acid catalyst is introduced into the mixing step and/or at the start of the hydroxylation reaction.

According to a first variant of the process of the invention, a complexing agent is added to stabilize the hydrogen peroxide.

According to another variant of the process of the invention, a cocatalyst is also used.

From a practical viewpoint, a preferred method for implementing the reagents consists in separately introducing the phenolic compound optionally supplemented with a complexing agent, optionally all or part of the acid catalyst and the hydrogen peroxide solution. The cocatalyst is also introduced separately.

The mixing operation is performed at a temperature that is sufficient for the starting phenol or phenol ether to remain liquid. Said temperature is chosen as a function of the melting point of the phenolic substrate. As regards phenol, for example, the mixing operation is performed at a temperature generally greater than 41 or even 42° C.

The mixing operation is performed such that the reaction does not start or starts very little during this step.

Thus, it is desirable for the degree of conversion of the hydrogen peroxide to be less than 25 mol %, preferably between 0.5 mol % and 25 mol % and even more preferentially between 0.5 mol % and 15 mol %.

To do this, the temperature of this mixing operation is advantageously chosen to be not more than 85° C. and preferably between 45° C. and 60° C.

The temperature during the mixing operation is chosen differently depending on whether the catalyst is introduced during this mixing step or at the start of the hydroxylation.

Specifically, when it is introduced, totally or partly, during the mixing, it is desirable, in order to minimize the degree of conversion of the hydrogen peroxide, to choose a lower temperature that is in the defined range preferentially between 45° C. and 60° C.

If the catalyst is totally introduced at the start of the hydroxylation reaction, the mixing operation may take place at a higher temperature, which may be up to 85° C.

The mixing may be performed at atmospheric pressure, but higher pressures may also be envisioned. For example, pressures of between 1 and 200 bar absolute may be suitable for use.

This step may be performed under an inert atmosphere, for example under nitrogen or under argon, nitrogen being preferred especially on account of its reduced cost.

The residence time and the temperature of the reaction medium in the mixing device must be appropriate for the chosen degree of conversion of hydrogen peroxide in said device.

After this mixing of the reagents, the hydroxylation reaction is performed.

It should be noted that during this reaction, the reaction medium is preferentially a one-phase system comprising a liquid phase, but the invention does not exclude gas-liquid two-phase systems.

According to one characteristic of the process of the invention, the hydroxylation reaction is performed under adiabatic conditions.

The heat evolved by the reaction suffices by itself to make the reaction proceed, without it being necessary to perform any external temperature regulation.

Thus, the reaction is performed in a reactor which has the characteristic of being thermally insulated from the exterior, such that it is performed under adiabatic conditions. Given the exothermicity of the reaction, the temperature increases naturally in the reactor.

It may be a reactor made of an insulating material such as various PVDF (polyvinylidene fluoride), PVC (polyvinyl chloride) or PTFE (polytetrafluoroethylene) polymers, which is optionally filled, for example with carbon or glass fiber. A vitrified steel or glass reactor may also be suitable for use.

Another means for insulating the reactor, especially in the case of reactors with a metallic framework, is to lag it, so as to avoid any thermal exchange with the exterior.

Lagging may be done by wrapping the reactor in lagging such as glass wool, rockwool or insulating synthetic foam, especially polyurethane foam, the lagging optionally being covered with a metallic coating, for example made of ordinary or stainless steel.

The reaction may be performed at atmospheric pressure, but higher pressures may also be envisioned as mentioned previously.

It is also possible to perform this step under an inert atmosphere, preferably a nitrogen atmosphere.

At the end of the reaction, the hydroxylation product may be either separated from the unconverted substrate and, where appropriate, the catalysts and cocatalysts via the usual means, especially by distillation and/or liquid/liquid extraction, and conveyed to the reaction zone, or directly engaged in a step which uses it as starting substrate.

In accordance with an embodiment variant of the invention, the mixing of the reagents and the hydroxylation reaction are performed simultaneously.

To do this, at least the phenolic compound is preheated to a temperature above 70° C., preferably between 70° C. and 85° C., before performing the reaction under adiabatic conditions.

The phenolic compound and the hydrogen peroxide solution may be used separately.

The acid catalyst may be introduced separately, in total or in part, at the start of the reaction.

It is also possible to prepare premixes of reagents, phenolic substrate and hydrogen peroxide solution: the catalyst then being introduced separately.

In the case of the presence of a complexing agent, this agent may be introduced, for example, into the phenolic substrate.

In this variant, at least the phenolic compound is preheated, but it is also optionally possible to preheat the other reagents such as the hydrogen peroxide solution and the acid catalyst.

The reaction is performed as described above under adiabatic conditions.

According to a preferred embodiment of the invention, the reagents are mixed together in a mixing device equipped with a stirrer and heating means, and the hydroxylation is then performed under adiabatic conditions in a piston-flow reactor.

According to another embodiment of the invention, the step of mixing of the reagents and the hydroxylation step are performed under adiabatic conditions in a piston-flow reactor.

In this case, the fluids (at least the phenolic substrate) must be preheated in order to initiate the reaction.

According to another embodiment of the invention, the second step of the process, namely the hydroxylation, is performed in a succession of at least two piston-flow reactors maintained under adiabatic conditions and separated by a heat exchanger.

Specifically, to limit any overoxidation leading to the formation of heavy products, it may be useful to perform the hydroxylation in several stages and thus several steps may be envisioned.

Thus, the hydroxylation reaction is started in adiabatic mode and the reaction mixture obtained is subjected to cooling by passing through a heat exchanger so as to lower its temperature by 5° C. to 90° C. and preferably by 10° C. to 40° C.

The hydroxylation is continued in a second section by conveying said mixture into a second adiabatic reactor, and so on.

Finally, according to another embodiment of the invention, the reagents are mixed together in a mixing device equipped with a stirrer and heating means, and the hydroxylation second step is performed in an array of piston-flow reactors mounted in parallel.

Advantageously, at least one piston-flow reactor is used to implement the process of the invention.

The term "piston flow" defines a unidirectional flow in which, in a plane perpendicular to the flow, all the fluid streams travel with a uniform speed. In such a flow, the radial mixing is perfect, whereas there is no axial mixing. In practice, these conditions are considered as being met when the flow is turbulent.

It is estimated that a flow is turbulent when the Reynolds number is greater than or equal to 5000 and preferentially when it is greater than 10 000. When the flow is not turbulent, the radial mixing is not perfect and there may be axial back-mixing. In this case, for a Reynolds number of less than about 5000 and more particularly less than 2000, the tubular reactor or the column reactor is packed with baffles and/or is structured.

It is recalled that the definition of the Reynolds number is:

$$Re = \frac{\rho \cdot v \cdot d}{\mu}$$

in which:
  $\rho$ is the mass per unit volume of the fluid in kg/m$^3$;
  v is the flow rate in m/s;
  d is the diameter of the reactor in m;
  $\mu$ is the dynamic viscosity in Pa·s
  Generally, Re is between 1 and 1 000 000.

According to preferred embodiments, the piston-flow reactor in which the hydroxylation reaction is performed is a tubular reactor or a column reactor.

In the description that follows of the present invention, the term "tubular reactor" means a reactor in the form of a tube, and the term "column reactor" means a vertical reactor of circular cross section.

The invention will be understood more clearly on reading the description that follows, which is given purely as an example, and made with reference to the attached drawings 1 to 7.

A first practical embodiment of the invention is illustrated by the attached drawing in the form of FIG. 1. FIG. 1 is a schematic view of apparatus suitable for implementing the invention, and which comprises two assemblies.

A first assembly comprises a jacketed stirred reactor (1) equipped with means for introducing the reagents.

The second assembly comprises a piston-flow reactor (2).

At the outlet of the stirred reactor (1), a reaction mixture is obtained, which is introduced into the piston-flow reactor (2).

Figure 2:
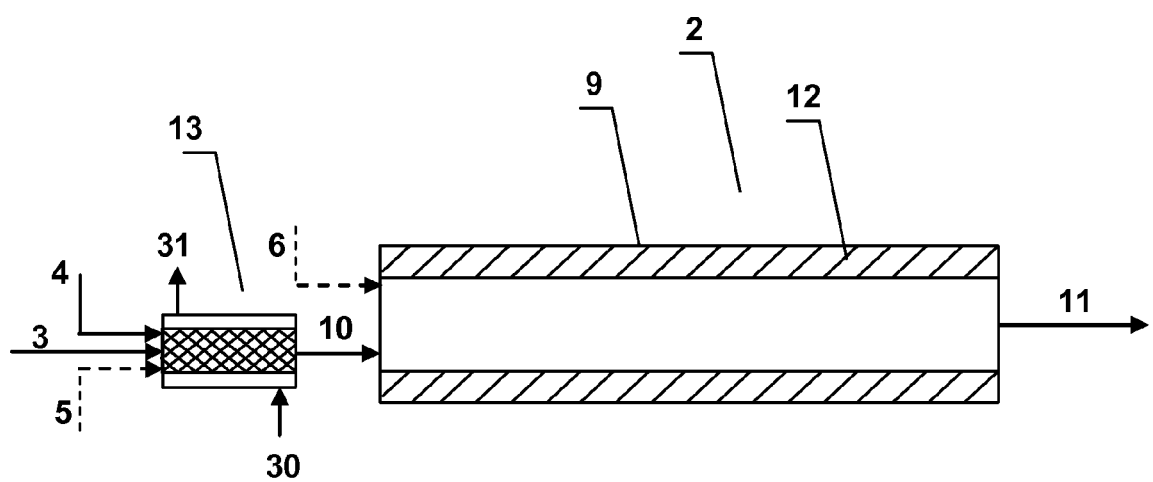
FIG. 2 is a schematic view of an apparatus suitable for implementing the process of the invention, which comprises, as in FIG. 1, two assemblies, but which differs only in that the jacketed stirred reactor is replaced with a jacketed static mixer heated via a heat-exchange fluid circulating in a jacket.

FIG. 2 is a schematic view of apparatus which comprises, as in FIG. 1, two assemblies, but which differs only in that the jacketed stirred reactor is replaced with a jacketed static mixer (13) heated via a heat-exchange fluid circulating in a jacket, which enters at (30) and exits at (31).

Figure 3:
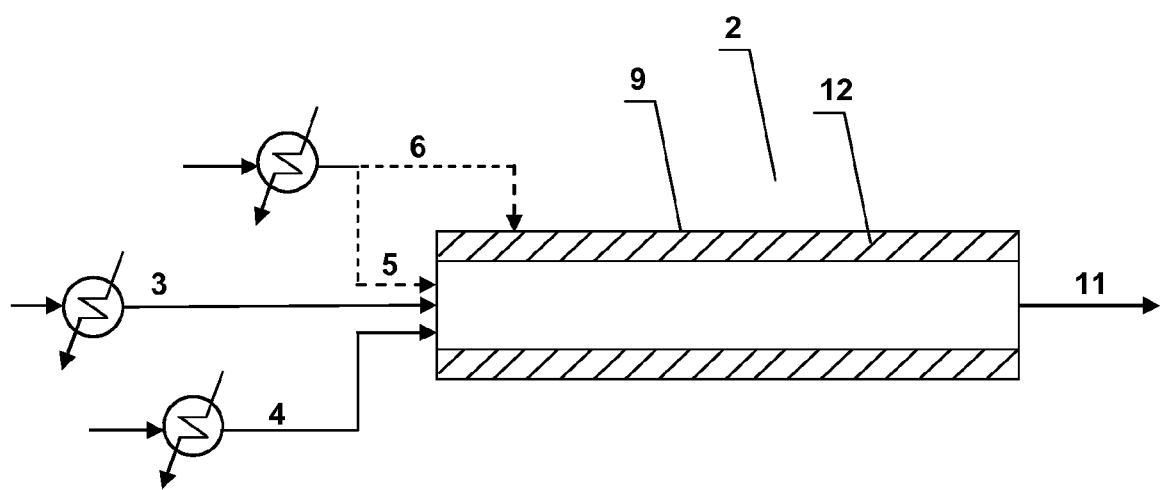
FIG. 3 illustrates a piston-flow reactor equipped with means for introducing the reagents suitable for implementing the process of the invention, according to which the mixing of the various reagents is performed at the inlet of the piston-flow reactor.

Another embodiment of the invention is shown by the attached drawing in the form of FIG. 3. The equipment lies in a piston-flow reactor (2) equipped with means for introducing the reagents.

The reagents, which are optionally preheated by passage through a heat exchanger, are introduced into the piston-flow reactor (2).

Figure 4:
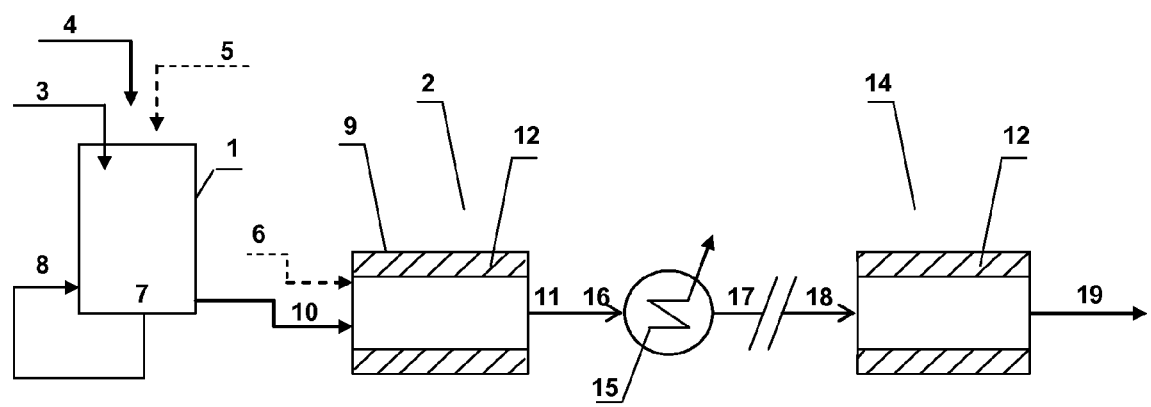
FIG. 4 is a schematic view of apparatus suitable for performing a variant of the process of the invention in which the hydroxylation step is performed such that the reaction temperature is staged in at least two piston-flow reactors working under adiabatic conditions.

FIG. 4 is a schematic view of apparatus suitable for performing a variant of the process of the invention in which the installation is configured such that the reaction temperature is staged.

The apparatus used consists of several assemblies.

The first assembly comprises the reactor (1) equipped with means for introducing the reagents and for mixing.

The second assembly comprises at least two piston-flow reactors (2) and (14) separated by a heat exchanger.

On exiting the stirred reactor (1) a reaction mixture is obtained, which is introduced into the piston-flow adiabatic reactor (2) and then passes through the heat exchanger, in which it is cooled via a heat-exchange fluid (15) and subsequently introduced into the piston-flow reactor (14).

On exiting reactor (19), the hydroxylated product is obtained.

According to preferred embodiments, the reactor in which the hydroxylation reaction is performed is a tubular reactor or a column reactor.

FIG. 5 is a schematic view of apparatus which comprises, as in FIG. 1, two assemblies, but which differs only in that the piston-flow reactor is replaced with an array of piston-flow reactors mounted in parallel.

FIGS. 6 and 7 illustrate types of piston-flow reactors that may be used in the process of the invention.

FIG. 6 is a schematic representation of a tubular reactor formed from concentric tubes.

FIG. 7 is a schematic representation of a reactor in column form.

A more detailed account of the means of the invention is given with reference to FIGS. 1 to 7, which schematically show the steps of the process of the invention, without, however, limiting the scope of the invention thereto.

According to various embodiments of the invention, the mixing and hydroxylation steps may be performed:
  successively, i.e. the reaction mixture prepared in a first container equipped with heating means, then passes into the piston-flow reactor,
  or simultaneously, i.e. the reagents are mixed together and immediately subjected to the hydroxylation step by introduction into the piston-flow reactor: one or more of the reagents being preheated by passing through a heat exchanger before being introduced into said reactor.

FIGS. 1 and 2 illustrate the process of the invention in which the mixture of the reagents is prepared in a mixing device before being introduced into the piston-flow reactor.

The mixture of the reagents may be stirred and heated in this mixing device.

The jacketed stirred reactor represented in FIG. 1) and the jacketed static mixer (13) are examples of mixing devices, but other types may be used, as mentioned below.

A first class of mixing devices concerns mechanically stirred reactors. The reactor is generally of vertical cylindrical form with a flat or elliptical base.

This reactor is equipped with means for introducing the reagents, heating means, a stirring system, and, at the bottom or top, a system for withdrawing the reaction mixture. The reactor is also equipped with a device for measuring the temperature and pressure.

The mixing is performed in a reactor which has good performance qualities in terms of material transfer and heat transfer.

The stirring system, not shown in FIG. 1, may be a rotary stirrer.

Examples of stirrers that may be mentioned include, inter alia, a turbine with straight or inclined paddles or a marine impeller or any mobile "hydrofoil".

A second class of mixing device concerns external loops. The mixing of the reaction medium then takes place by circulation in a loop of a fraction or all of the contents of the reactor, mechanically stirred or not, with the aid of a pump on an external loop.

A third class of mixing device illustrated by FIG. 2 combines mixers without a rotating part, known as dynamic mixers, on the one hand, and static mixers, on the other hand.

In the family of dynamic mixers, mention may be made of tangential jet mixers, impact jet mixers, or ejectors.

For the "static" mixers, various interiors may be listed, such as the static mixers (Sulzer SMX, Kenics, etc.), a bulk bed of beads or particles, metallic or ceramic foams, etc.

All these mixers force the streams of fluids fed in to exchange matter with each other by dividing into substreams or by creating small-scale structures. These structures increase the contact surface between the flows of reagents.

The exchange surface for the heat transfer may be increased by means of coils or plates present inside the reactor or via a heat-exchange fluid circulating in a jacket.

Heat-exchange fluids that may be mentioned include, inter alia, water, steam or a suitable organic solvent, for instance an aromatic ether such as diphenyl ether and/or benzyl ether, a silicone oil, a paraffin and/or naphthenic oil, petroleum distillation residues, etc.

From a practical viewpoint, the phenolic substrate (3) and a hydrogen peroxide solution (4) are introduced into the jacketed stirred reactor (1) according to FIG. 1 or into the static mixer (13) according to FIG. 2.

In the case of the presence of a complexing agent, this agent may be introduced, for example, into the phenolic substrate.

A cocatalyst feed device may also be envisioned.

The catalyst is introduced at (5) or optionally at the top (6) of the piston-flow reactor.

The catalyst may also be introduced at (5) and (6).

The various reagents are introduced gradually, preferably continuously, their rate of introduction being regulated by means of a pump.

The mixture of reagents is obtained as mentioned previously and FIG. 1 illustrates the production of the mixture by establishing a recirculation loop as illustrated in FIG. 1.

Part of the reaction mixture is withdrawn at the bottom of the reactor at (7) and is then introduced into the reactor at (8): the forced circulation of the mixture being ensured by a pump, not shown in the drawing.

According to FIG. 2, the reagents are mixed together by means of the very structure of the static mixer.

Heating is ensured by circulating a heat-exchange fluid in a jacket.

As mentioned previously, the mixing is performed under conditions such that the reaction is minimized.

Thus, the temperature of this mixing operation is advantageously chosen to be not more than 85° C. and preferably between 45° C. and 60° C.

The reaction is advantageously performed at atmospheric pressure, but higher pressures may also be envisioned. For example, pressures of between 1 and 200 bar absolute may be suitable for use.

This step may advantageously be performed under an inert atmosphere, for example under nitrogen or under argon, nitrogen being preferred especially on account of its reduced cost.

The residence time and the temperature of the reaction medium in the mixing device must be appropriate for the chosen degree of conversion of hydrogen peroxide in said device.

The reaction mixture then passes from reactor (1) to reactor (2) according to FIG. 1 or from the mixer (13) to the reactor (2) according to FIG. 2, by gravitational flow or by forced circulation, for example using a pump, usually a centrifugal pump.

In accordance with the process of the invention, a second step relative to the hydroxylation reaction is performed in a piston-flow reactor (2).

The reactor consists of a tube (9) through which circulate the reaction mixture which enters at (10) and the reaction products which leave at (11).

The reactor has the characteristic of being lagged. It is surrounded by a lagging coat (12).

Usually, the reactor will have a length/diameter ratio of greater than 3. It may especially be a tubular reactor with a length/diameter ratio of between 4 and 30 and in particular between 5 and 10.

Advantageously, the tubular reactor is formed so as to have low bulk and makes it possible to increase the piston nature, for example when it is pushed back.

The material of the reactor is not particularly limited. It will be chosen so as to be inert under the reaction conditions, lagged or made of polymer, which has both the advantage of avoiding corrosion and the advantage of conserving the heat of the reaction in the reaction medium.

Tubular reactors are generally arranged horizontally.

However, in order to adapt to the space constraints, it may also be envisioned to provide a reactor arranged vertically or inclined.

Advantageously, one or more perforated plates are arranged close to the reagent inlet so as to ensure good homogeneity of the fluids in this section of the reactor.

Advantageously, the tubular reactor is in column form. It is equipped with reagent inlet and reaction mixture outlet pipes.

The reagents are fed into reactor (1) via standard means, for instance a pump and more particularly a centrifugal pump or a volumetric pump.

In principle, it is preferable to work in the liquid phase only.

The tubular reactor may be equipped with baffles.

The presence of baffles in the reactor creates turbulence which ensures homogeneity of the reaction mixture throughout the entire section of the reactor. The baffles thus make it possible to maintain the piston-flow nature, including the case of a Reynolds number of less than 5000.

The material of the baffles is unimportant, provided that it is chemically inert with respect to the reaction mixture under the reaction conditions. Generally, they are made of materials such as glass, metal, especially stainless steel, carbon, polymer or ceramic.

Various types of baffle may be envisioned. They may especially be:
  bulk baffles, which consist of small objects, for example in the form of rings, stools, balls or cylinders which are hollow, with which all or part of the reactor is filled.
  structured baffles: pins, static mixers, chicanes.

Preferably, the baffles are arranged in the reactor close to the reagent inlet.

In the case of a reactor arranged vertically, the baffles are preferably arranged along the entire top of the reactor. It is then necessary to provide a suitable support, for example in the form of crossbeams, so as to hold the baffles in place.

Packing of static mixer type, composed of mixing elements comprising guide blades arranged at precise angles and positioned in a complex manner, is particularly preferred. This type of packing is sold, for example, by the company Sulzer under the names SMV and SMX.

For the description of these baffles, reference may be made to the article *Don't Be Baffled By Static Mixers* published in Chemical Engineering, May 2003.

From a practical point of view, a linear tube without baffles, folded back on itself and arranged horizontally or vertically when the Reynolds number is greater than 2000 and preferentially when it is greater than 5000, is chosen.

When the Reynolds number is less than 5000, a reactor without baffles may be used, by structuring it. For example, it is possible to fold the tubular reactor back on itself in the form of a helix or a succession of bends/straight lines; this structure may optionally be partially equipped with baffles. After each bend of the tube, a section of baffles of an equivalent length is inserted, for example from 3 to 6 times the diameter of the tube, over all or part of the straight length of the tube located between two successive bends.

In this step of the process, the temperature is not controlled since the conditions are adiabatic.

Given the exothermicity of the reaction, it is pointed out as a guide that the reaction temperature at the inlet of the piston-flow reactor is above 70° C. and preferably between 70° C. and 85° C.

The reaction is advantageously performed at atmospheric pressure, but higher pressures may be envisioned as previously.

Specifically, at high temperature, and thus toward the reactor outlet, it may arise that the phenolic substrate vaporizes partially: it is then less available to be converted. To operate under pressure, the reactor is equipped either with a laboratory-scale or pilot-scale pressure-release valve or with a regulating valve downstream of the reactor, in order to adjust the pressure to the desired value.

This step may advantageously be performed under an inert atmosphere, preferably under a nitrogen atmosphere.

At the end of the reaction, the hydroxylated product present in the reaction mixture is recovered at (11).

FIG. 3 illustrates a method for implementing the process of the invention, according to which the mixing of the various reagents is performed at the inlet of the piston-flow reactor.

The phenolic substrate (3) and the hydrogen peroxide solution (4) may be introduced separately into the reactor.

The acid catalyst may be introduced separately at the inlet of the reactor (5) and/or further inside, at the start of reactor (6) as shown in FIG. 3.

It is also possible to prepare premixes of reagents, phenolic substrate and hydrogen peroxide solution: the catalyst may then be introduced separately at the inlet of the reactor (5) and/or further inside at the start of reactor (6).

In the case of the presence of a complexing agent, this agent may be introduced, for example, into the phenolic substrate.

The cocatalyst may also be added separately.

According to this embodiment, at least the phenolic substrate needs to be preheated before being introduced into the reactor (2).

It is also optionally possible to preheat the other reagents such as the hydrogen peroxide solution and the acid catalyst.

The preheating temperature is advantageously chosen to be above 70° C. and preferably between 70° C. and 85° C.

Preheating of the reagents is performed by passage through a heat exchanger.

The reagents, of which at least the phenolic substrate is preheated, are introduced into the piston-flow reactor having characteristics as described for FIG. 1.

A reaction mixture (11) comprising the hydroxylated product is recovered at the outlet of reactor (2).

FIG. 4 illustrates a method for implementing the process of the invention, according to which a first step of mixing of the reagents is performed in the mixing device (1), and the hydroxylation step is then performed such that the reaction temperature is staged in at least two piston-flow reactors working under adiabatic conditions.

For the first step, in an identical manner as illustrated by FIG. 1), the phenolic substrate (3) and a hydrogen peroxide solution (4) are introduced into the mixing device (1).

In the case of the presence of a complexing agent, this agent may be introduced, for example, into the phenolic substrate.

A cocatalyst feed device may also be envisioned.

The catalyst is introduced at (5) or optionally at the top (6) of the piston-flow reactor.

At the outlet of the mixing device, the mixture of reagents (10) is introduced into a succession of at least two piston-flow reactors separated by a heat exchanger.

In this embodiment, the reactors always function adiabatically, but with different thermal zones.

Each stage comprises a piston-flow reactor and a heat exchanger: the installation ending with a piston-flow reactor.

The number of stages may range, for example, from 2 to 100 and preferably from 2 to 10.

The temperature in each stage is determined according to the desired degree of conversion of the hydrogen peroxide.

FIG. 4 represents, as an illustration, an assembly comprising at least two piston-flow reactors (2) and (14) separated by a heat exchanger (15). The different temperatures in each stage are provided by the presence of a heat exchanger whose function is to cool the reaction mixture at the outlet of a first reactor before it enters the next, so as to maximize the conversion of the phenolic substrate while at the same time minimizing its overoxidation into heavy products.

The temperature staging and the residence time of each zone are established to be appropriate for the reaction performance qualities (degree of conversion and yields).

This determination may be made in accordance with the publication by J. Villermaux (*Génie de la réaction chimique; conception et fonctionnement des réacteurs* [Chemical reaction engineering: design and functioning of reactors]; J. Villermaux; Tec & Doc Lavoisier; 1993) or that by O. Levenspiel (*Chemical Reaction Engineering;* $2^{nd}$ edition; Wiley Int.; 1972).

The staging of the temperature in the process according to the invention is thus performed by virtue of the presence of the heat exchangers between the reactors.

With reference to FIG. 4, which illustrates one embodiment, the reaction mixture (10) passes through the piston-flow reactor (2) and at its outlet (11) is introduced at (16) into a heat exchanger (15).

The cooled or condensed reaction mixture (17) leaving the heat exchanger (17) is introduced at (18) into the next piston-flow reactor (14).

The mixture at the outlet (19) comprises the hydroxylated product.

It is therefore possible to envision adding a succession of piston-flow reactors and heat exchangers.

The reaction is advantageously performed at atmospheric pressure, but higher pressures of between 1 and 200 bar absolute may also be envisioned as previously.

This step may advantageously be performed under an inert atmosphere.

FIG. 5 illustrates a method for implementing the process of the invention, according to which a first step of mixing of the reagents is performed in the mixing device (1), and the hydroxylation step is then performed in an array of piston-flow reactors mounted in parallel and working under adiabatic conditions.

For the first step, in an identical manner as illustrated by FIG. 1), the phenolic substrate (3) and a hydrogen peroxide solution (4) are introduced into the mixing device (1).

In the case of the presence of a complexing agent, this agent may be introduced, for example, into the phenolic substrate.

A cocatalyst feed device may also be envisioned.

The catalyst is introduced at (5) or optionally at the top (6) of each piston-flow reactor.

At the outlet of the mixing device, the mixture of reagents (10) is divided according to FIG. 5 into three fractions: each fraction being introduced into a piston-flow reactor (32), (33) and (34) functioning adiabatically.

In this embodiment, the number of piston-flow reactors is 3 in FIG. 5, but may range, for example, from 2 to 100.

At the outlet of each reactor, a reaction mixture is recovered comprising the hydroxylated product: the three flows exiting the reactors being combined at (11).

The attached FIGS. 6 and 7 illustrate the types of apparatus that may be used as piston-flow reactor.

FIG. 6 shows a tubular reactor formed from concentric tubes.

Thus, the reactor consists of a tube (20) through which circulate the reaction mixture which enters at (21) and the reaction products which leave at (22).

The tube is lagged (23).

The tube may contain packing sections after each bend (24).

FIG. 7 shows a reactor in column form (25) which is lagged (26).

The column is equipped with baffles (27).

The reaction mixture is introduced at (27) and the products leave at (28).

As mentioned previously, the process of the invention makes it possible to obtain a significant increase in the production efficiency of the apparatus.

The process of the invention may be performed in a piston-flow reactor or in apparatus combining in sequence a mixing device in which the mixing of the reagents takes place and a piston-flow reactor in which the hydroxylation reaction is performed.

An advantage of the process of the invention, performing the hydroxylation reaction of the phenolic substrate in a piston-flow reactor, affords a gain in selectivity when compared with a process in which the hydroxylation reaction is performed in a cascade of stirred reactors. Specifically, good selectivity was obtained on account of a limitation of the subsequent reactions.

Another advantage of the process of the invention is that the degree of conversion of the phenolic substrate is increased, for example ranging from 5% to 15% and preferentially from 5% to 10%, such that the amount of residual phenolic substrate to be recycled is reduced, thus making it possible to lower the energy consumption.

According to the embodiment of the invention in apparatus comprising a mixing device coupled to a piston-flow reactor, the mixing of the reagents upstream of the piston-flow reactor in a device separate from said piston-flow reactor makes it possible to increase the safety of the process, and it is then possible to make use of more concentrated aqueous hydrogen peroxide solutions whose concentration may range from 30% to 90% by weight and preferably from 30% to 70%.

Moreover, the fact that there is only one mixing device coupled to a piston-flow reactor presents the advantage of low bulk and also a saving in operating, energy and investment costs when compared with a cascade of perfectly stirred reactors, each equipped with means for introducing the reagents, for removing the products, and also devices for mixing the reagents and for controlling the process parameters.

Another advantage of the invention is that it leads to good reaction yields.

The invention will be explained in greater detail by means of examples that illustrate the invention without, however, limiting it.

In the examples, the following abbreviations have the meanings as follows:

The degree of conversion ($DC_{H2O2}$) of hydrogen peroxide corresponds to the ratio between the number of moles of hydrogen peroxide converted and the number of moles of hydrogen peroxide introduced.

The degree of conversion ($DC_{phenol}$) of phenol corresponds to the ratio between the number of moles of phenol converted and the number of moles of phenol introduced.

The diphenol reaction yield ($RY_{diphenols}$) corresponds to the ratio between the number of moles of diphenols formed (pyrocatechol+hydroquinone) and the number of moles of hydrogen peroxide introduced.

The pyrocatechol reaction yield ($RY_{pyrocatechol}$) corresponds to the ratio between the number of moles of pyrocatechol formed and the number of moles of hydrogen peroxide introduced.

The hydroquinone reaction yield ($RY_{hydroquinone}$) corresponds to the ratio between the number of moles of hydroquinone formed and the number of moles of hydrogen peroxide introduced.

The diphenol selectivity ($TY_{diphenols}$) corresponds to the ratio between the number of moles of diphenols formed (pyrocatechol+hydroquinone) and the number of moles of hydrogen peroxide transformed.

The ratio PC/HQ is defined by the ratio between the number of moles of pyrocatechol and the number of moles of hydroquinone.

EXAMPLE 1

The example is performed in a type of apparatus as illustrated by FIG. 1.

The following are introduced at 50° C. continuously, with the aid of pumps, into a jacketed reactor with a working volume of 150 mL, equipped with a stirring system of the type with 4 inclined paddles, an ascending condenser, a nitrogen inlet and a temperature regulation system:

883 g/h (9.38 mol/h) of phenol containing pyrophosphoric acid in a proportion of 400 ppm by mass relative to the phenol, perchloric acid in a proportion of 400 mol ppm relative to the phenol, 26.0 g/h of hydrogen peroxide at 70% by weight (i.e. 0.53 mol/h of hydrogen peroxide).

The passage time through this reactor is 10 minutes; the medium being maintained at 50° C.

The reaction medium of this reactor is introduced continuously using a pump into an exchanger in which it is heated to 80° C. and then into a tubular reactor packed with Sulzer SMX mixers with an overall volume of 57 mL (length=200 mm; diameter=19 mm); this reactor being lagged and maintained under pressure by a flap valve tared at an outlet pressure of 10 bar. The passage time in the exchanger is about 20 seconds.

After a stabilization time (about 30 minutes), the diphenols formed are assayed by high-performance liquid chromatography and the hydrogen peroxide is assayed by potentiometry.

The results obtained at the outlet of the tubular reactor are given in table (I).

EXAMPLE 2

The following are introduced at 50° C. continuously, with the aid of pumps, into a jacketed reactor with a working volume of 150 mL, equipped with a stirring system of the type with 4 inclined paddles, an ascending condenser, a nitrogen inlet and a temperature regulation system:

831 g/h (8.83 mol/h) of phenol containing pyrophosphoric acid in a proportion of 400 ppm by mass relative to the phenol, perchloric acid in a proportion of 400 mol ppm relative to the phenol, 34.3 g/h of hydrogen peroxide at 70% by weight (i.e. 0.706 mol/h of hydrogen peroxide).

The passage time through this reactor is 11 minutes; the medium being maintained at 50° C.

The reaction medium of this reactor is introduced continuously using a pump into an exchanger in which it is heated to 80° C. and then into a tubular reactor packed with Sulzer SMX mixers with an overall volume of 57 mL (length=200 mm; diameter=19 mm); this reactor being lagged and maintained under pressure by a flap valve tared at an outlet pressure of 10 bar. The passage time in the exchanger is about 20 seconds.

After a stabilization time (about 30 minutes), the diphenols formed are assayed by high-performance liquid chromatography and the hydrogen peroxide is assayed by potentiometry.

The results obtained at the outlet of the tubular reactor are given in table (I).

EXAMPLE 3

Comparative

The following are introduced at 50° C. continuously, with the aid of pumps, into a jacketed reactor with a working volume of 30 mL, equipped with a stirring system of the type with 4 inclined paddles, an ascending condenser, a nitrogen inlet and a heating device:

130 g/h of phenol containing pyrophosphoric acid in a proportion of 400 ppm by mass relative to the phenol, perchloric acid in a proportion of 400 mol ppm relative to the phenol, 5.4 g/h of hydrogen peroxide at 70% by weight (i.e. 0.110 mol/h of hydrogen peroxide).

The passage time in this reactor is about 14 minutes.

The reaction medium of this reactor is introduced continuously, with the aid of a pump, into a jacketed tubular reactor packed with Sulzer SMX mixers, with an overall volume of 57 mL (length=200 mm; diameter=19 mm), and whose temperature is set at 110° C. This temperature corresponds to the average of the temperatures of the adiabatic reactor of example 2.

After a stabilization time (about 1.5 hours), the diphenols formed are assayed by high-performance liquid chromatography and the hydrogen peroxide is assayed by potentiometry.

The results obtained at the outlet of the tubular reactor are given in table (I).

TABLE I

| Example ref. | 1 | 2 | 3, comparative |
|---|---|---|---|
| Type of reactor | 1 stirred reactor at 50° C. + 1 adiabatic piston reactor | 1 stirred reactor at 50° C. + 1 adiabatic piston reactor | 1 stirred reactor at 50° C. + 1 piston reactor at a 110° C. isotherm |
| Catalyst | $HClO_4$ | $HClO_4$ | $HClO_4$ |
| $HClO_4$/PhOH (mol ppm) | 400 | 400 | 400 |
| Pyrophosphoric acid/PhOH (ppm by weight) | 400 | 400 | 400 |
| $H_2O_2$/PhOH (mol %) | 5.7 | 8.0 | 8.0 |
| Residence time (min) | 4 | 4 | 26 |
| Inlet temperature (° C.) | 80 | 80 | 110 |
| Outlet temperature (° C.) | 143 | 170 | 110 |
| DC PhOH | 5.1% | 6.9% | 7.0% |
| RY HQ | 31% | 27% | 30% |
| RY PC | 48% | 45% | 46% |
| RY (diphenols) | 78% | 72% | 76% |
| Production (diphenols) (g/h) | 46.1 | 56.1 | 9.2 |
| Ratio PC/HQ | 1.55 | 1.64 | 1.54 |
| DC $H_2O_2$ | 99% | 99% | 99% |
| TY (diphenols)/$H_2O_2$ | 79% | 72% | 76% |
| Cooling thermal charge (kcal/h) | 0 | 0 | 2.7 |

This table shows that working under adiabatic conditions rather than isothermal conditions makes it possible to substantially reduce the passage time in the reactor.

The production efficiency is consequently greatly improved, even though a slight drop in selectivity is observed: for the same reactor, the adiabatic reaction makes it possible to multiply the production of diphenols by a factor of 6 relative to the same test under isothermal conditions.

Finally, the adiabatic reaction has the advantage of not requiring any cooling, in contrast with the isothermal reactor.

EXAMPLE 4

The following are introduced at 50° C. continuously, with the aid of pumps, into a jacketed reactor with a working volume of 50 mL, equipped with a stirring system of the type with 4 inclined paddles, an ascending condenser, a nitrogen inlet and a temperature regulation system:

182 g/h (1.94 mol/h) of phenol containing pyrophosphoric acid in a proportion of 400 ppm by mass relative to the phenol, perchloric acid in a proportion of 400 mol ppm relative to the phenol, 17.6 g/h of hydrogen peroxide at 30% by weight (i.e. 0.15 mol/h of hydrogen peroxide).

The passage time through this reactor is 15 minutes, and the medium is maintained at 50° C.

The reaction medium of this reactor is introduced continuously using a pump into an exchanger in which it is heated to 80° C. and then into a tubular reactor packed with Sulzer SMX mixers with an overall volume of 284 mL (length=1000 mm; diameter=19 mm); this reactor being lagged and maintained under pressure by a flap valve tared at an outlet pressure of 10 bar. The passage time in the exchanger is about 1 minute 30 seconds.

After a stabilization time (about 3 hours), the diphenols formed are assayed by high-performance liquid chromatography and the hydrogen peroxide is assayed by potentiometry.

The results obtained at the outlet of the tubular reactor are given in table (II).

TABLE II

| Example Reference | 2 | 4 |
|---|---|---|
| Type of reactor | 1 stirred reactor at 50° C. + 1 adiabatic piston reactor 70% $H_2O_2$ | 1 stirred reactor at 50° C. + 1 adiabatic piston reactor 30% $H_2O_2$ |
| Catalyst | $HClO_4$ | $HClO_4$ |
| $HClO_4$/PhOH (mol ppm) | 400 | 400 |
| Pyrophosphoric acid/PhOH (ppm by weight) | 400 | 400 |
| $H_2O_2$/PhOH (mol %) | 8.0 | 8.0 |
| Residence time (min) | 4 | 89 |
| Inlet temperature (° C.) | 80 | 80 |
| Outlet temperature (° C.) | 170 | 170 |
| DC PhOH | 6.9% | 6.9% |
| RY HQ | 27% | 28% |
| RY PC | 45% | 45% |
| RY (diphenols) | 72% | 73% |
| Production (diphenols) (g/h) | 56.1 | 9.2 |
| Ratio PC/HQ | 1.64 | 1.61 |
| DC $H_2O_2$ | 99% | 99% |
| TY (diphenols)/$H_2O_2$ | 72% | 73% |
| Cooling thermal charge (kcal/h) | 0 | 0 |

This table shows that the use of 30 weight % aqueous hydrogen peroxide solution greatly increases the reaction time without any significant change in the selectivities, when compared with the use of 70 weight % aqueous hydrogen peroxide solution.

The invention claimed is:

1. A process for hydroxylating a phenol or a phenol ether, by reacting said phenol or phenol ether with hydrogen peroxide, in the presence of an acid catalyst, said process comprising the following steps performed successively or simultaneously:
    a first step of mixing a phenolic substrate selected from the group consisting of a phenol and a phenol ether, with a hydrogen peroxide solution under conditions such that the temperature is sufficient for the starting phenolic substrate selected from the group consisting of a phenol and a phenol ether to remain liquid and for the degree of conversion of the hydrogen peroxide to be less than 25% by mol,
    a second step consisting in performing a hydroxylation reaction of the phenolic substrate with hydrogen peroxide under adiabatic conditions to form a hydroxylated product; the acid catalyst being introduced into the mixing step and/or at the start of the hydroxylation reaction, and
    optionally, a third step of recovery of the hydroxylated product.

2. The process as claimed in claim 1, wherein said temperature of the mixing operation is chosen to be not more than 85° C.

3. The process as claimed in claim 1, wherein said mixing is performed at atmospheric pressure or at higher pressures.

4. The process as claimed in claim 1, wherein said mixing step is performed by separately introducing:
    the phenolic substrate optionally supplemented with a complexing agent;
    optionally all or part of the acid catalyst;
    the hydrogen peroxide solution; and
    optionally a cocatalyst.

5. The process as claimed in claim 1, wherein said hydroxylation reaction is performed in a reactor which is thermally insulated from the exterior, said reactor being made of an insulating material and/or being lagged.

6. The process as claimed in claim 5, wherein said reactor is selected from the group consisting of:
    a reactor made of PVDF (polyvinylidene fluoride), PVC (polyvinyl chloride) or PTFE (polytetrafluoroethylene) polymer, optionally filled with carbon or glass fiber; or made of vitrified steel or glass,
    a reactor lagged with glass wool, rockwool or insulating synthetic foam,
    the lagging of said reactor optionally being covered with a metallic coating; and
    any combinations thereof.

7. The process as claimed in claim 1, wherein, when the mixing step and the hydroxylation reaction step are performed simultaneously, and wherein at least the phenolic substrate is preheated to a temperature above 70° C.

8. The process as claimed in claim 1, wherein said phenolic substrate and said hydrogen peroxide solution are mixed together in a mixing device equipped with a stirrer and heating means, and wherein the hydroxylation reaction is performed under adiabatic conditions in a piston-flow reactor.

9. The process as claimed in claim 7, whereon said mixing step and said hydroxylation step are performed under adiabatic conditions in a piston-flow reactor.

10. The process as claimed in claim 1, wherein said phenolic substrate and said hydrogen peroxide solution are mixed together in a mixing device equipped with a stirrer and heating means, and wherein the hydroxylation second step is performed in a succession of at least two piston-flow reactors maintained under adiabatic conditions and separated by a heat exchanger.

11. The process as claimed in claim 1, wherein said phenolic substrate and said hydrogen peroxide solution are mixed together in a mixing device equipped with a stirrer and heating means, and wherein the hydroxylation second step is performed in an array of piston-flow reactors mounted in parallel.

12. The process as claimed in claim 8, wherein said mixing device is selected from the group consisting of:
    a mechanically stirred reactor;
    a reactor, mechanically stirred or not, with a loop for circulation of a fraction or all of the contents of said reactor, with the aid of a pump on an external loop;
    a dynamic mixer; and
    a static mixer.

13. The process as claimed in claim 12, wherein in said mixing device equipped with said stirring and heating means, the exchange surface for heat transfer is increased by means of coils or plates present inside said reactor or via a heat-exchange fluid circulating in a jacket.

14. The process as claimed in claim 8, wherein said piston-flow reactor is a tubular reactor which has a length/diameter ratio of greater than 3.

15. The process as claimed in claim 8, wherein said piston-flow reactor is a tubular reactor formed from concentric tubes or a reactor in the form of a column.

16. The process as claimed in claim 1, wherein said phenolic substrate corresponds to the general formula (I):

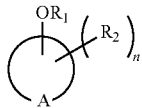

wherein

A symbolizes a benzene or naphthalene ring, $R_1$ is a hydrogen atom or a substituent selected from the group consisting of an alkyl group, a cycloalkyl group, an aryl group, and an aralkyl group, $R_2$ represents a hydrogen atom or one or more identical or different substituents, n, which is the number of substituents per aromatic ring, is less than or equal to 4.

17. The process as claimed in claim 16, wherein said phenolic substrate corresponds to the general formula (Ia):

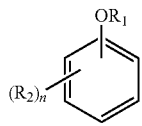

in said formula (I)a:

n is a number from 0 to 4, $R_1$ is a substituent selected from the group consisting of a hydrogen atom, an alkyl group, a cycloalkyl group, an aryl group, and an aralkyl group, $R_2$, which is identical or different, is a substituent selected from the group consisting of an alkyl group, an alkoxy group, a hydroxyl group, a halogen atom, a haloalkyl group, and a perhaloalkyl group.

18. The process as claimed in claim 17, wherein said phenolic substrate is selected from the group consisting of phenol, o-cresol, m-cresol, p-cresol, anisole, phenetole, 2-methoxyphenol (guaiacol), and 2-ethoxyphenol (guetol).

19. The process as claimed in claim 1, wherein said acid catalyst is a strong protic acid with a pKa in water of less than −0.1 or a mixture of protic acids.

20. The process as claimed in claim 19, wherein said acid catalyst is selected from the group consisting of sulfuric acid, perchloric acid, methanesulfonic acid, trifluoromethanesulfonic acid, toluenesulfonic acid, phenolsulfonic acid, bis-trifluoromethanesulfonimide, a mixture of perchloric acid and sulfuric acid; a mixture of perchloric acid and 4-hydroxybenzenesulfonic acid; a mixture of trifluoromethanesulfonic acid and 4-hydroxybenzenesulfonic acid; and a mixture of bis-trifluoromethanesulfonimide and 4-hydroxybenzenesulfonic acid.

21. The process as claimed in claim 1, wherein said hydroxylation of said phenolic substrate is further performed in the presence of a cocatalyst, said cocatalyst being a ketone compound corresponding to formula (II):

wherein in said formula (II):

$R_a$ and $R_b$, which are identical or different, represent hydrocarbon-based groups containing from 1 to 30 carbon atoms or together form a divalent group, optionally substituted with one or more halogen atoms or functional groups that are stable under the reaction conditions, X represents a valency bond, a —CO— group, a —CHOH group, or a group —$(R)_n$— in which R represents an alkylene group and n is an integer chosen between 1 and 16.

22. The process as claimed in claim 21, wherein said ketone compound corresponds to formula (IIa) below:

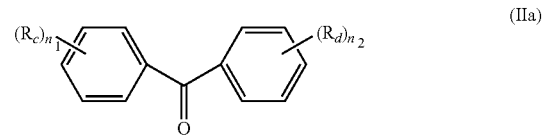

wherein in said formula (IIa):

$R_c$ and $R_d$, which are identical or different, represent a hydrogen atom or a substituent, $n_1$ and $n_2$, which are identical or different, represent a number equal to 0, 1, 2 or 3, optionally, wherein the two carbon atoms located a to the two carbon atoms bearing the —CO group are linked together via a valency bond or via a —$CH_2$— group, thus forming a ketone ring, which is saturated or unsaturated.

23. The process as claimed in claim 1, being performed in the presence of an agent for complexing transition metal ions, which is stable under the reaction conditions.

* * * * *